United States Patent [19]

Ohno et al.

[11] Patent Number: 4,961,875
[45] Date of Patent: Oct. 9, 1990

[54] CONDENSATE OF AN OPTICALLY ACTIVE-4-(1-HYDROXYETHYL)BIPHENYL WITH AN OPTICALLY ACTIVE ORGANIC ACID

[75] Inventors: Kouji Ohno; Hiromichi Inoue; Shinichi Saito; Kazutoshi Miyazawa; Makoto Ushioda, all of Kanagawaken, Japan

[73] Assignee: Chisso Corporation, Osaka, Japan

[21] Appl. No.: 284,118

[22] Filed: Dec. 14, 1988

[30] Foreign Application Priority Data

Dec. 15, 1987 [JP] Japan .................... 62-317000

[51] Int. Cl.$^5$ .................. C09K 19/12; C09K 19/52; G02F 1/13; C07C 29/66
[52] U.S. Cl. .................... 252/299.66; 252/299.01; 252/299.6; 350/350 S; 560/187; 560/255
[58] Field of Search .............. 252/299.01, 299.66; 350/350 S; 560/187, 255

[56] References Cited

U.S. PATENT DOCUMENTS 4,744,918  5/1988  Heppke et al. ............ 252/299.61
4,882,084 11/1989  Ohno et al. ............... 252/299.66

FOREIGN PATENT DOCUMENTS 255219  2/1988  European Pat. Off. .
270243  6/1988  European Pat. Off. .

Primary Examiner—John S. Maples
Assistant Examiner—Philip Tucker
Attorney, Agent, or Firm—Wenderoth, Lind & Ponack

[57] ABSTRACT

A liquid crystalline, optically active compound useful as a component of various liquid crystal compositions, a liquid crystal composition containing the same and a light switching element using the liquid crystal composition are provided, which liquid crystalline, optically active compound is expressed by the formula

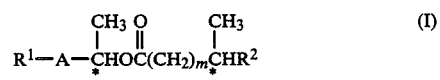

wherein $R^1$ is 1-18C alkyl or alkoxy, $R^2$ is 2-18C alkyl or 1-18C alkoxy, A is

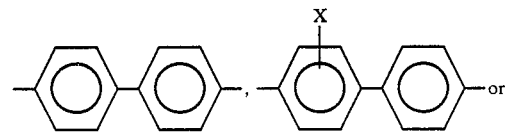 , or

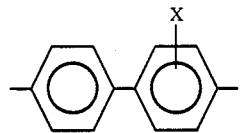

wherein X is halogen or CN, m is 0 to 12, and * indicates an asymmetric carbon atom.

8 Claims, No Drawings

CONDENSATE OF AN OPTICALLY ACTIVE-4-(1-HYDROXYETHYL)BIPHENYL WITH AN OPTICALLY ACTIVE ORGANIC ACID

BACKGROUND OF THE INVENTION

1. Field of the Invention

This invention relates to an optically active compound useful in the fields of liquid crystal display elements or liquid crystal light switching elements, and a liquid crystal composition containing the same. More particularly it relates to a novel liquid crystalline compound having optically active groups and a liquid crystal composition containing the same, and exhibiting a chiral nematic phase or chiral smectic phase.

In addition, the liquid crystalline compound referred to herein is not limited only to compounds having a liquid crystal state which can be observed by themselves, but also it includes substances which, even when no liquid crystal state can be observed by themselves, have a chemical structure similar to that of the former and also are useful as an additive.

2. Description of the Related Art

It is well known that the importance of optically active substances in liquid crystal compositions used for electrooptical elements utilizing liquid crystal phases, i.e. liquid crystal elements or liquid crystal light switching elements, consists in the usefulness of constituting components of (i) cholesteric phase (chiral nematic phase) and
(ii) chiral smectic phase.

It is also well known that the cholesteric phase (Ch phase) may be composed of as main components, compounds which exhibit Ch phase by themselves, but also may be composed by adding optically active substances to nematic phase and in the latter case, it is unnecessary that the added optically active substances exhibit liquid crystal phases by themselves. It is also known that Ch phase is utilized for display elements utilizing cholesteric-nematic phase transition, and besides, Ch phase is also utilized in place of nematic phase in order to prevent the so-called reverse domain from occurring. Further, optically active substances have been used as a constituting component of cholesteric liquid crystal compositions used for STN mode (a mode having the twist angle of liquid crystals enlarged up to 180°-270°) which is one of relatively new display modes; thus the importance of optically active substances has been more and more increasing.

On the other hand, an electrooptical element using chiral smectic liquid crystals has recently been noted. This element utilizes ferroelectricity of liquid crystals and this novel display mode has a possibility of notably improving the response rate (Clark et al, Applied Phys. lett., 36, 899 (1980)). This display mode is directed to a method utilizing chiral smectic phases exhibiting ferroelectricity such as chiral smectic C phase (hereinafter abbreviated to SC* phase). Ferroelectricity-exhibiting phases are not limited to SC* phase, but chiral smectic F, G, H, I and the like phases have been known to also exhibit ferroelectricity. When these ferroelectric liquid crystals are used for display elements, liquid crystal materials exhibiting ferroelectric liquid crystal phases within a broad temperature region including room temperature have been desired. At present, however, no single compound which satisfies such a requirement has been known; thus liquid crystal compositions which satisfy such required characteristics as much as possible have been prepared and used.

Chiral smectic liquid crystal compositions may also be composed of, as their main component, compounds which exhibit a chiral smectic phase by themselves, as in the case of the Ch phase, but the composition may also be composed by adding optically active substances to smectic phase and in this case, too, it is unnecessary that the added optically active substances exhibit liquid crystal phases by themselves.

SUMMARY OF THE INVENTION

The present inventors have searched for various compounds in order to find liquid crystalline, optically active compounds useful as a component of the above-mentioned liquid crystal compositions, and have achieved the present invention.

The present invention in a first aspect resides in a compound expressed by the formula $$R^1-A-\overset{*}{\underset{|}{C}}H-O-\overset{O}{\underset{\|}{C}}-(CH_2)_m-\overset{*}{\underset{|}{C}}HR^2 \quad (I)$$
$$\phantom{R^1-A-}\overset{|}{CH_3}\phantom{-O-C-(CH_2)_m-}\overset{|}{CH_3}$$

wherein $R^1$ represents an alkyl group or an alkoxy group each of 1 to 18 carbon atoms, $R^2$ represents an alkyl group of 2 to 18 carbon atoms or an alkoxy group of 1 to 18 carbon atoms, —A— represents

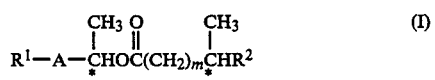

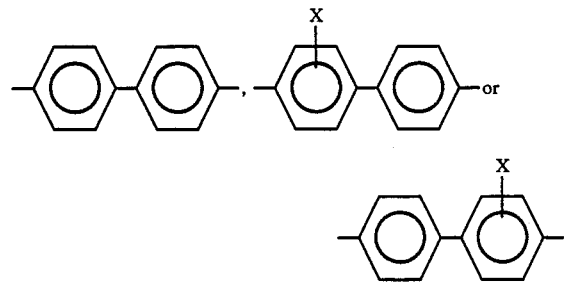

wherein X represents a halogen atom or cyano group, m represents an integer of 0 to 12 and * indicates an asymmetric carbon atom.

The present invention in a second aspect resides in a liquid crystal composition containing at least one member of the above-mentioned compounds of the formula (I), particularly a chiral smectic liquid crystal composition.

The present invention in a third aspect resides in an electrooptical element using the above-mentioned liquid crystal composition.

DETAILED DESCRIPTION OF PREFERRED EMBODIMENTS $R^1$ in the formula (I) is preferably an alkyl group or an alkoxy group each of 3 to 16 carbon atoms, more preferably an alkyl group or an alkoxy group each of 5 to 10 carbon atoms.

$R^2$ is preferably an alkyl group of 2 to 12 carbon atoms or an alkoxy group of 1 to 12 carbon atoms, more preferably an alkyl group of 2 to 8 carbon atoms or an alkoxy group of 1 to 6 carbon atoms.

The optically active compounds of the present invention mostly exhibit no liquid crystal properties by themselves, but when they are used as a component of ferroelectric liquid crystal compositions, it is possible to enhance the spontaneous polarization value Ps of the compositions.

Here, the importance of the spontaneous polarization value will be described. In general, the response time $\tau$ of ferroelectric liquid crystal display elements is expressed by the following equation (II):

$$\tau = \frac{\eta}{Ps \cdot E} \quad \text{(II)}$$

wherein $\eta$: viscosity and E: intensity of electric field. As apparent from the equation (II), reduction in the response time is effected by increasing the Ps or by reducing the viscosity.

When the compound of the present invention is used as a component of ferroelectric liquid crystal compositions even if it exhibits no liquid crystal phase, it has a function of notably increasing the Ps of the ferroelectric liquid crystal compositions and as a result, it is possible to shorten the response time. As will be described later in an Example, for example when a compound of the present invention

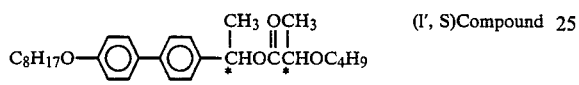

(1', S)Compound is added in an amount of 10% by weight to a liquid crystal composition exhibiting achiral smectic C phase (which composition exhibits no spontaneous polarization), a ferroelectric liquid crystal composition having a large spontaneous polarization value is obtained, which has a response time as short as 55 μsec at 25° C. (see Example 4).

This composition was compared with a liquid crystal composition obtained by adding an optically active compound disclosed in Japanese patent application laid-open No. Sho 63-126842/1988,

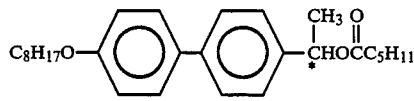

in an amount of 10% by weight to the above-mentioned achiral smectic C liquid crystal composition. As a result, the response time of the former was 55 μsec, whereas that of the latter was 100 μsec under the same conditions. As seen from this fact, when the compound of the present invention is used, it is possible to prepare a composition having a very short response time.

Further, when the compound of the formula (I) of the present invention is added to a liquid crystal composition exhibiting chiral smectic C phase, but having a very small Ps value, it is possible to raise the Ps value up to a practical value. In short, it can be said that the compound of the present invention is far superior as a component bearing the Ps of ferroelectric liquid crystal compositions.

Further, since the compound of the formula (I) of the present invention has optically active carbon atoms, it has a capability of inducing a twist structure by adding the compound to nematic liquid crystals. Nematic liquid crystals having a twist structure, i.e. chiral nematic liquid crystals, do not form the so-called reverse domain (stripe pattern) of TN mode display elements; hence the compound of the formula (I) is usable as an agent for preventing the reverse domain from occurring.

Chiral nematic liquid crystal compositions obtained by adding the compound of the present invention to nematic liquid crystals have short chiral pitches; hence the compound of the present invention is useful as an agent for adjusting the chiral pitch.

Further, the temperature dependency of pitch (δP) expressed by the equation $$\delta P = \frac{2(P(t_1) - P(t_2))}{P(t_1) + P(t_2)} \times \frac{100}{t_1 - t_2}$$

wherein $P(t_1)$ and $P(t_2)$ represent pitch length (μm) measured at $t_1$°C. and $t_2$°C., respectively, was very large as shown later in Example 2.

The compound of the present invention may be prepared, e.g. through the following route:

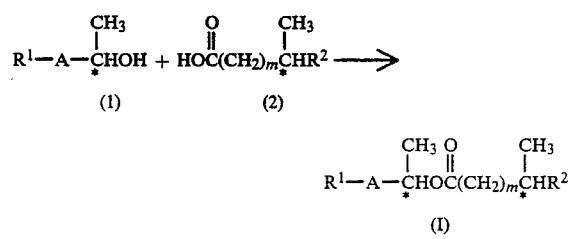

Namely, compound (1) is reacted with compound (2) to obtain a compound expressed by the formula (I).

Here, as to the absolute configuration of the compound of the formula (I), if the absolute configuration of the d compound (1) having a plus rotatory polarization is expressed by d' and that of the l compound (1) is expressed by l', the compound of the formula (I) of d' and that of l' are obtained from the above-mentioned d compound and l compound, respectively.

The compound and composition of the present invention will be described in more detail by way of Examples.

EXAMPLE 1

Preparation of (1l',2S)-4-(1-(2-butoxypropionyloxy)ethyl)-4'-octyloxybiphenyl (a compound of the formula (I) wherein R¹ represents octyloxy group, R² represents butoxy group, —A— represents

m represents 0 and the absolute configuration of the asymmetric carbons is (1l',2S))

1'-4-(1-Hydroxyethyl)-4'-octyloxybiphenyl prepared according to the process disclosed in Japanese patent application laid-open No. Sho 63-126836/1988 ($[\alpha]_d^{25°}$ −27.0° (C 1.0, CHCl₃), m.p. 124° C.) (5 g) was dissolved in dichloromethane (200 ml), followed by dissolving in the solution, N,N'-dicyclohexylcarbodiimide (hereinafter abbreviated to DCC) (5.4 g) and 4-N,N-dimethylaminopyridine (hereinafter abbreviated to DMAP) (1.0 g), adding 2-butoxypropionic acid (4.8 g) to the resulting solution, agitating the mixture at room temperature for 6 hours, filtering off deposited crystals, washing the filtrate with 6N-hydrochloric acid, then with 2N-NaOH aqueous solution and further with water until the washing water became neutral, distilling off the solvent and recrystallizing the residue from ethanol to obtain the objective compound (5.7 g) ($[\alpha]_D^{23.5°} -96.1°$ (C 1.28, $CHCl_3$)). M.P.: 30° C.

EXAMPLE 2

Example 1 was repeated except that l'-4-octyloxy-4'-(1-hydroxyethyl)biphenyl was replaced by d'-4-octyloxy-4'-(1-hydroxyethyl)biphenyl ($[\alpha]_D^{23.5°} +29.8°$ (C 1.14, $CHCl_3$), m.p. 125° C.) to obtain (1d',2S)-4-(1-(2-butoxypropionyloxy)ethyl)-4'-octyloxybiphenyl (3.2 g) ($[\alpha]_D^{23.5°} +42.3°$ (C 1.42, $CHCl_3$). M.P.: 18° C.

Concrete examples of the compound of the formula (I) prepared in the same manner as in Example 1 or Example 2 are listed as follows:

(1l',2S)-4-(1-(2-Methoxypropionyloxy)ethyl)-4'-pentylbiphenyl oil at r.t.
(1l',2S)-4-(1-(2-Ethoxypropionyloxy)ethyl)-4'-pentylbiphenyl
(1l',2S)-4-(1-(2-Propoxypropionyloxy)ethyl)-4'-pentylbiphenyl
(1d',2S)-4-(1-(2-Pentyloxypropionyloxy)ethyl)-4'-pentylbiphenyl
(1l',2S)-4-(1-(2-Hexyloxypropionyloxy)ethyl)-4'-pentylbiphenyl
(1l',2S)-4-(1-(2-Heptyloxypropionyloxy)ethyl)-4'-pentylbiphenyl
(1l',2S)-4-(1-(2-Octyloxypropionyloxy)ethyl)-4'-pentylbiphenyl
(1d',2S)-4-(1-(2-Methoxypropionyloxy)ethyl)-4'-hexylbiphenyl
(1l',2S)-4-(1-(2-Ethoxypropionyloxy)ethyl)-4'-hexylbiphenyl
(1l',2S)-4-(1-(2-Propoxypropionyloxy)ethyl)-4'-hexylbiphenyl
(1l',2S)-4-(1-(2-Butoxypropionyloxy)ethyl)-4'-hexylbiphenyl
(1l',2R)-4-(1-(2-Pentyloxypropionyloxy)ethyl)-4'-hexylbiphenyl
(1l',2S)-4-(1-(2-Hexyloxypropionyloxy)ethyl)-4'-hexylbiphenyl
(1l',2S)-4-(1-(2-Heptyloxypropionyloxy)ethyl)-4'-hexylbiphenyl
(1d',2S)-4-(1-(2-Octyloxypropionyloxy)ethyl)-4'-hexylbiphenyl
(1l',2S)-4-(1-(2-Methoxypropionyloxy)ethyl)-4'-heptylbiphenyl
(1l',2S)-4-(1-(2-Ethoxypropionyloxy)ethyl)-4'-heptylbiphenyl
(1l',2S)-4-(1-(2-Propoxypropionyloxy)ethyl)-4'-heptylbiphenyl
(1l',2S)-4-(1-(2-Butoxypropionyloxy)ethyl)-4'-heptylbiphenyl
(1l',2R)-4-(1-(2-Pentyloxypropionyloxy)ethyl)-4'-heptylbiphenyl
(1l',2S)-4-(1-(2-Hexyloxypropionyloxy)ethyl)-4'-heptylbiphenyl
(1d',2S)-4-(1-(2-Heptyloxypropionyloxy)ethyl)-4'-heptylbiphenyl
(1l',2S)-4-(1-(2-Octyloxypropionyloxy)ethyl)-4'-heptylbiphenyl
(1l',2S)-4-(1-(2-Methoxypropionyloxy)ethyl)-4'-octylbiphenyl
(1l',2S)-4-(1-(2-Ethoxypropionyloxy)ethyl)-4'-octylbiphenyl
(1l',2S)-4-(1-(2-Propoxypropionyloxy)ethyl)-4'-octylbiphenyl
(1d,2S)-4-(1-(2-Butoxypropionyloxy)ethyl)-3'-cyano-4'-octylbiphenyl
(1l',2S)-4-(1-(2-Pentyloxypropionyloxy)ethyl)-4'-octylbiphenyl
(1l',2S)-4-(1-(2-Hexyloxypropionyloxy)ethyl)-4'-octylbiphenyl
(1l',2R)-4-(1-(2-Heptyloxypropionyloxy)ethyl)-4'-octylbiphenyl
(1l',2S)-4-(1-(2-Octyloxypropionyloxy)ethyl)-4'-octylbiphenyl
(1l',2S)-4-(1-(2-Methoxypropionyloxy)ethyl)-4'-pentyloxybiphenyl
(1l',2S)-4-(1-(2-Ethoxypropionyloxy)ethyl)-4'-pentyloxybiphenyl
(1l',2S)-4-(1-(2-Propoxypropionyloxy)ethyl)-3'-cyano-4'-pentyloxybiphenyl
(1l',2S)-4-(1-(2-Butoxypropionyloxy)ethyl)-4'-pentyloxybiphenyl
(1l',2S)-4-(1-(2-Pentyloxypropionyloxy)ethyl)-4'-pentyloxybiphenyl
(1l',2R)-4-(1-(2-Hexyloxypropionyloxy)ethyl)-4'-pentyloxybiphenyl
(1l',2S)-4-(1-(2-Heptyloxypropionyloxy)ethyl)-4'-pentyloxybiphenyl
(1l',2S)-4-(1-(2-Octyloxypropionyloxy)ethyl)-4'-pentyloxybiphenyl
(1l',2S)-4-(1-(2-Methoxypropionyloxy)ethyl)-4'-hexyloxybiphenyl
(1l',2S)-4-(1-(2-Ethoxypropionyloxy)ethyl)-4'-hexyloxybiphenyl
(1l',2R)-4-(1-(2-Propoxypropionyloxy)ethyl)-4'-hexyloxybiphenyl
(1l',2S)-4-(1-(2-Butoxypropionyloxy)ethyl)-4'-hexyloxybiphenyl
(1d',2S)-4-(1-(2-Heptyloxypropionyloxy)ethyl)-4'-hexyloxybiphenyl
(1l',2S)-4-(1-(2-Octyloxypropionyloxy)ethyl)-4'-hexyloxybiphenyl
(1l',2S)-4-(1-(2-Methoxypropionyloxy)ethyl)-4'-heptyloxybiphenyl
(1l',2S)-4-(1-(2-Ethoxypropionyloxy)ethyl)-4'-heptyloxybiphenyl
(1l',2R)-4-(1-(2-Propoxypropionyloxy)ethyl)-4'-heptyloxybiphenyl
(1l',2S)-4-(1-(2-Butoxypropionyloxy)ethyl)-4'-heptyloxybiphenyl
(1l',2S)-4-(1-(2-Pentyloxypropionyloxy)ethyl)-4'-heptyloxybiphenyl
(1d',2R)-4-(1-(2-Hexyloxypropionyloxy)ethyl)-4'-heptyloxybiphenyl
(1l',2S)-4-(1-(2-Heptyloxypropionyloxy)ethyl)-4'-heptyloxybiphenyl
(1l',2S)-4-(1-(2-Octyloxypropionyloxy)ethyl)-4'-heptyloxybiphenyl
(1l',2S)-4-(1-(2-Methoxypropionyloxy)ethyl)-4'-octyloxybiphenyl
(1d',2S)-4-(1-(2-Ethoxypropionyloxy)ethyl)-4'-octyloxybiphenyl
(1l',2R)-4-(1-(2-Propoxypropionyloxy)ethyl)-4'-octyloxybiphenyl
(1l',2S)-4-(1-(2-Butoxypropionyloxy)ethyl)-4'-octyloxybiphenyl m.p. 30° C. (Example 1)
(1d',2S)-4-(1-(2-Butoxypropionyloxy)ethyl)-4'-octyloxybiphenyl m.p. 18° C. (Example 2)
(1l',2S)-4-(1-(2-Pentyloxypropionyloxy)ethyl)-4'-octyloxybiphenyl (1l',2S)-4-(1-(2-Hexyloxypropionyloxy)ethyl)-4'-octyloxybiphenyl
(1l',2S)-4-(1-(2-Heptyloxypropionyloxy)ethyl)-4'-octyloxybiphenyl
(1l',2S)-4-(1-(2-Octyloxypropionyloxy)ethyl)-4'-octyloxybiphenyl
(1l',2S)-4-(1-(2-Methylbutanoyloxy)ethyl)-3'-fluoro-4'-pentylbiphenyl
(1l',2S)-4-(1-(2-Methylbutanoyloxy)ethyl)-4'-pentylbiphenyl
(1l',3S)-4-(1-(3-Methylpentanoyloxy)ethyl)-3-cyano-4'-pentylbiphenyl
(1l',2S)-4-(1-(2-Methylpentanoyloxy)ethyl)-4'-pentylbiphenyl
(1d',4S)-4-(1-(4-Methylhexanoyloxy)ethyl)-4'-pentylbiphenyl
(1l',4S)-4-(1-(4-Methylhexanoyloxy)ethyl)-4'-pentylbiphenyl
(1l',6S)-4-(1-(6-Methyloctanoyloxy)ethyl)-4'-pentylbiphenyl
(1l',5S)-4-(1-(5-Methylheptanoyloxy)ethyl)-4'-pentylbiphenyl
(1d',2S)-4-(1-(2-Methylbutanoyloxy)ethyl)-4'-hexylbiphenyl
(1l',2S)-4-(1-(2-Methylpentanoyloxy)ethyl)-4'-hexylbiphenyl
(1l',3S)-4-(1-(3-Methylpentanoyloxy)ethyl)-3'-bromo-4'-hexylbiphenyl
(1l',4S)-4-(1-(4-Methylhexanoyloxy)ethyl)-4'-hexylbiphenyl
(1l',5S)-4-(1-(5-Methyloctanoyloxy)ethyl)-4'-hexylbiphenyl
(1l',6S)-4-(1-(6-Methylnonanoyloxy)ethyl)-4'-hexylbiphenyl
(1l',7S)-4-(1-(7-Methyldodecanoyloxy)ethyl)-4'-hexylbiphenyl
(1d',5S)-4-(1-(5-Methyldecanoyloxy)ethyl)-4'-hexylbiphenyl
(1l',2S)-4-(1-(2-Methylbutanoyloxy)ethyl)-4'-heptylbiphenyl
(1l',2S)-4-(1-(2-Methylbutanoyloxy)ethyl)-3-cyano-4'-heptylbiphenyl
(1l',3S)-4-(1-(3-Methylpentanoyloxy)ethyl)-4'-heptylbiphenyl
(1l',3S)-4-(1-(3-Methylhexanoyloxy)ethyl)-4'-heptylbiphenyl
(1l',4S)-4-(1-(4-Methylhexanoyloxy)ethyl)-4'-heptylbiphenyl
(1l',4S)-4-(1-(4-Methylheptanoyloxy)ethyl)-4'-heptylbiphenyl
(1d',5S)-4-(1-(5-Methylheptanoyloxy)ethyl)-4'-heptylbiphenyl
(1l',5S)-4-(1-(5-Methylheptanoyloxy)ethyl)-3'-cyano-4'-heptylbiphenyl
(1l',2S)-4-(1-(2-Methylbutanoyloxy)ethyl)-4'-octylbiphenyl
(1l',2S)-4-(1-(2-Methylpentanoyloxy)ethyl)-4'-octylbiphenyl
(1l',3S)-4-(1-(3-Methylpentanoyloxy)ethyl)-4'-octylbiphenyl
(1d',4S)-4-(1-(4-Methylhexanoyloxy)ethyl)-4'-octylbiphenyl
(1l',5S)-4-(1-(5-Methylheptanoyloxy)ethyl)-4'-octylbiphenyl
(1l',2S)-4-(1-(2-Methylbutanoyloxy)ethyl)-3-cyano-4'-octylbiphenyl
(1l',2S)-4-(1-(2-Methylbutanoyloxy)ethyl)-3'-cyano-4'-octylbiphenyl
(1l',2S)-4-(1-(2-Methylbutanoyloxy)ethyl)-3-fluoro-4'-octylbiphenyl
(1l',2S)-4-(1-(2-Methylbutanoyloxy)ethyl)-4'-pentyloxybiphenyl
(1l',2S)-4-(1-(2-Methylbutanoyloxy)ethyl)-3'-cyano-4'-pentuloxybiphenyl
(1l',2S)-4-(1-(2-Methylbutanoyloxy)ethyl)-3'-fluoro-4'-pentyloxybiphenyl
(1l',3S)-4-(1-(3-Methylpentanoyloxy)ethyl)-4'-pentyloxybiphenyl
(1l',4S)-4-(1-(4-Methylhexanoyloxy)ethyl)-4'-pentyloxybiphenyl
(1l',5S)-4-(1-(5-Methylheptanoyloxy)ethyl)-4'-pentyloxybiphenyl
(1l',6S)-4-(1-(6-Methyloctanoyloxy)ethyl)-4'-pentyloxybiphenyl
(1l',2S)-4-(1-(2-Methylbutanoyloxy)ethyl)-4'-hexyloxybiphenyl
(1l',2S)-4-(1-(2-Methylbutanoyloxy)ethyl)-3-cyano-4'-hexyloxybiphenyl
(1l',2S)-4-(1-(2-Methylbutanoyloxy)ethyl)-3-fluoro-4'-hexyloxybiphenyl
(1l',3S)-4-(1-(3-Methylpentanoyloxy)ethyl)-4'-hexyloxybiphenyl
(1d',4S)-4-(1-(4-Methylhexanoyloxy)ethyl)-4'-hexyloxybiphenyl
(1l',5S)-4-(1-(5-Methylheptanoyloxy)ethyl)-4'-hexyloxybiphenyl
(1l',2S)-4-(1-(2-Methylbutanoyloxy)ethyl)-4'-heptyloxybiphenyl
(1l',2S)-4-(1-(2-Methylbutanoyloxy)ethyl)-3-cyano-4'-heptyloxybiphenyl
(1l',2S)-4-(1-(2-Methylbutanoyloxy)ethyl)-3-fluoro-4'-heptyloxybiphenyl
(1l',3S)-4-(1-(3-Methylpentanoyloxy)ethyl)-4'-heptyloxybiphenyl
(1l',4S)-4-(1-(4-Methylhexanoyloxy)ethyl)-4'-heptyloxybiphenyl
(1d',7S)-4-(1-(7-Methyldodecanoyloxy)ethyl)-4'-heptyloxybiphenyl
(1l',3S)-4-(1-(3-Methylpentanoyloxy)ethyl)-3'-cyano-4'-heptyloxybiphenyl
(1l',3S)-4-(1-(3-Methylpentanoyloxy)ethyl)-3'-fluoro-4'-heptyloxybiphenyl
(1l',2S)-4-(1-(2-Methylbutanoyloxy)ethyl)-4'-octyloxybiphenyl
(1d',3S)-4-(1-(3-Methylpentanoyloxy)ethyl)-4'-octyloxybiphenyl
(1l',3S)-4-(1-(3-Methylpentanoyloxy)ethyl)-3-fluoro-4'-octyloxybiphenyl
(1l',4S)-4-(1-(4-Methylhexanoyloxy)ethyl)-4'-octyloxybiphenyl
(1d',4S)-4-(1-(4-Methylhexanoyloxy)ethyl)-4'-octyloxybiphenyl
(1l',5S)-4-(1-(5-Methylheptanoyloxy)ethyl)-4'-octyloxybiphenyl
(1l',6S)-4-(1-(6-Methyloctanoyloxy)ethyl)-4'-octyloxybiphenyl
(1l',7S)-4-(1-(7-Methylnonanoyloxy)ethyl)-4'-octyloxybiphenyl
(1l',8S)-4-(1-(8-Methyldecanoyloxy)ethyl)-4'-octyloxybiphenyl

EXAMPLE 3 (USE EXAMPLE 1)

(1l', 2S)-4-(1-(2-butoxypropionyloxy)ethyl)-4'-octyloxybiphenyl prepared in Example 1 was added in an amount of 1% by weight to ZLI-1132 made by Merck Company to obtain a chiral nematic liquid crystal composition, and the chiral pitch of this composition was measured according to Cano wedge method to give 35.9 μm at 20° C. and 76.5 μm at 60° C.

Further, the temperature dependency of the chiral pitch (δP) was +1.807 in the range of 20° to 60° C.

EXAMPLE 4 (USE EXAMPLE 2)

A nematic liquid crystal composition consisting of

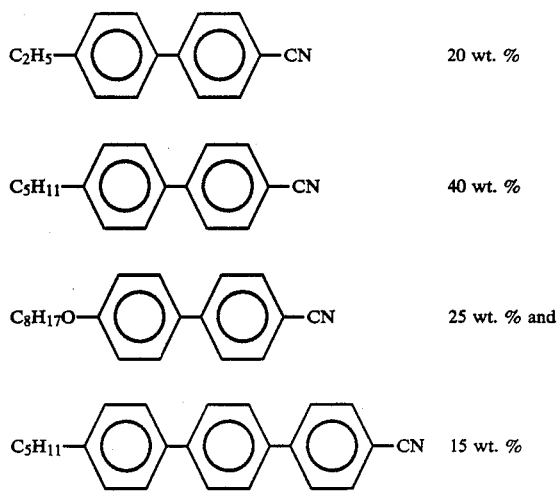

was filled in a cell provided with transparent electrodes each obtained by coating polyvinyl alcohol (PVA) as an aligning agent, followed by rubbing the resulting surface to subject it to a parallel aligning treatment, and having a distance between the electrodes of 10 μm to prepare a TN mode display cell, which was then observed under a polarizing microscope. As a result, a reverse domain was observed to be formed.

To the above nematic liquid crystal composition was added the compound of Example 1 as a compound of the present invention, i.e.

in an amount of 1% by weight, followed by similarly observing the mixture in a TN mode cell. As a result, the reverse domain was dissolved and a uniform nematic phase was observed.

EXAMPLE 5 (USE EXAMPLE 3)

An achiral smectic liquid crystal mixture consisting of

C$_6$H$_{13}$O—〈phenyl〉—〈pyrimidine(N,N)〉—C$_8$H$_{17}$   30 wt. %

C$_8$H$_{17}$O—〈phenyl〉—〈pyrimidine(N,N)〉—C$_8$H$_{17}$   20 wt. %

C$_9$H$_{19}$O—〈phenyl〉—〈pyrimidine(N,N)〉—C$_8$H$_{17}$   10 wt. %

C$_{10}$H$_{21}$O—〈phenyl〉—〈pyrimidine(N,N)〉—C$_8$H$_{17}$   10 wt. %

C$_5$H$_{11}$—〈phenyl〉—〈phenyl〉—〈pyrimidine(N,N)〉—C$_8$H$_{17}$   20 wt. % and

C$_7$H$_{15}$—〈phenyl〉—〈phenyl〉—〈pyrimidine(N,N)〉—C$_8$H$_{17}$   10 wt. % was prepared. This mixture had a m.p. of 4° C. exhibited SC phase at temperatures higher than the m.p. and nematic phase at 79° C. and formed isotropic liquid at 90° C.

To 90% by weight of this mixture was added the compound of Example 1 as a compound of the present invention (10% by weight) to prepare a chiral smectic liquid crystal composition. Its phase transition points were as follows: SC* phase at temperatures lower than 35° C., SA phase at 35° C., Ch phase at 70.2° C. and isotropic liquid at 80.8° C.

The composition was filled in a cell of 2 μm thickness provided with transparent electrodes each obtained by coating PVA as an aligning agent, followed by rubbing the resulting surface to subject it to a parallel aligning treatment to obtain a liquid crystal display element, which was then placed between crossed polarizer and analyzer, followed by impressing a voltage of ±10 V. As a result, change in the intensity of transmitted light was confirmed.

The response time was sought from the change in the intensity of transmitted light at that time to give about 55 μsec at 25° C.

The liquid crystal composition had a spontaneous polarization value of 4.0 nC/cm$^2$ at 25° C. and a tilt angle of 10.4°.

What we claim is:

1. A compound expressed by the formula $$R^1-A-\overset{*}{C}HOC(CH_2)_m\overset{*}{C}HR^2 \quad (I)$$
(with CH$_3$, O, CH$_3$ substituents on the indicated carbons)

wherein R$^1$ represents an alkyl group or an alkoxy group each of 5 to 10 carbon atoms, R$^2$ represents an alkoxy group of 1 to 6 carbon atoms, —A— represents 〈phenyl-phenyl〉—, —〈phenyl-phenyl(X)-phenyl〉— or -continued

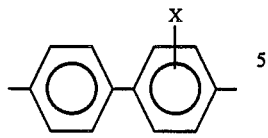

wherein X represents a halogen atom or cyano group, m represents an integer of 0 to 12 and * indicates an asymmetric carbon atom.

2. A compound according to claim 1 wherein said A represents

3. A compound according to claim 1 wherein said A represents

4. A compound according to claim 1 wherein said A represents

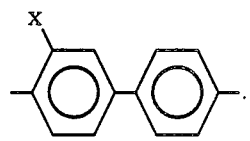

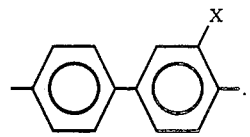

5. A liquid crystal composition comprising at least two components at least one of which is a compound as set forth in claim 1.

6. A liquid crystal composition according to claim 5 which exhibits a chiral smectic phase.

7. A liquid crystal composition according to claim 5 which exhibits a chiral nematic phase.

8. A light switching element using a liquid crystal composition as set forth in claim 5.

* * * * *